(12) United States Patent
Araki et al.

(10) Patent No.: US 10,088,446 B2
(45) Date of Patent: Oct. 2, 2018

(54) GAS SENSOR

(71) Applicant: DENSO CORPORATION, Kariya, Aichi-pref. (JP)

(72) Inventors: Takashi Araki, Kariya (JP); Keigo Mizutani, Nishio (JP)

(73) Assignee: DENSO CORPORATION, Kariya (JP)

( * ) Notice: Subject to any disclaimer, the term of this patent is extended or adjusted under 35 U.S.C. 154(b) by 139 days.

(21) Appl. No.: 15/315,738

(22) PCT Filed: Jun. 4, 2015

(86) PCT No.: PCT/JP2015/066161
§ 371 (c)(1),
(2) Date: Dec. 2, 2016

(87) PCT Pub. No.: WO2015/186776
PCT Pub. Date: Dec. 10, 2015

(65) Prior Publication Data
US 2017/0115250 A1    Apr. 27, 2017

(30) Foreign Application Priority Data

Jun. 4, 2014 (JP) .................................. 2014-115994

(51) Int. Cl.
*G01N 27/41* (2006.01)
*G01N 27/407* (2006.01)
(Continued)

(52) U.S. Cl.
CPC .......... *G01N 27/41* (2013.01); *G01M 15/104* (2013.01); *G01N 27/4072* (2013.01); *G01N 27/416* (2013.01)

(58) Field of Classification Search
CPC .. G01N 27/419; G01N 27/47; G01N 27/4072; G01N 27/416; G01N 27/404;
(Continued)

(56) References Cited

U.S. PATENT DOCUMENTS

| 5,763,763 A | 6/1998 | Kato et al. |
| 6,551,497 B1 | 4/2003 | Gao et al. |

(Continued)

FOREIGN PATENT DOCUMENTS

| JP | 2003-149199 | 5/2003 |
| JP | 2004-251626 | 9/2004 |

(Continued)

*Primary Examiner* — Gurpreet Kaur
(74) *Attorney, Agent, or Firm* — Nixon & Vanderhye P.C.

(57) ABSTRACT

A gas sensor device is equipped with a pump cell and a sensor cell. The pump cell works to regulate the concentration of oxygen in a measurement gas space. The sensor cell works to measure an oxygen ion current flowing between a sensor electrode and a reference electrode. The gas sensor device is designed to subtract the oxygen ion current value I2, as measured by the sensor cell a given period of time after spraying of fuel into the internal combustion engine is interrupted, from the oxygen ion current value I1, as measured by the sensor cell when the fuel is being sprayed into the internal combustion engine, to derive the concentration of a given gas component based on the corrected oxygen ion current value I. This results in improved accuracy in determining the concentration of the given gas component.

3 Claims, 7 Drawing Sheets

(51) Int. Cl.
*G01N 27/416* (2006.01)
*G01M 15/10* (2006.01)

(58) Field of Classification Search
CPC .. G01N 27/405; G01N 27/406; F02D 41/123; F02D 41/1454; F02D 41/146; G01M 15/104; G01M 15/10; G01M 15/102
See application file for complete search history.

(56) References Cited

U.S. PATENT DOCUMENTS

| | | | |
|---|---|---|---|
| 2002/0104758 A1* | 8/2002 | Mizutani | G01N 27/419 204/427 |
| 2004/0111868 A1 | 6/2004 | Katafuchi et al. | |
| 2016/0223488 A1 | 8/2016 | Kayama et al. | |

FOREIGN PATENT DOCUMENTS

| | | |
|---|---|---|
| JP | 2009-150719 | 7/2009 |
| JP | 2009-175013 | 8/2009 |
| JP | 2011-058834 | 3/2011 |

\* cited by examiner

GAS SENSOR

This application is the U.S. national phase of International Application No. PCT/JP2015/066161 filed 4 Jun. 2015, which designated the U.S. and claims priority to JP Patent Application No. 2014-115994 filed 4 Jun. 2014, the entire contents of each of which are hereby incorporated by reference.

TECHNICAL FIELD

The present invention generally relates to a gas sensor device which works to measure the concentration of a given gas component contained in exhaust gas flowing in an exhaust pipe of an internal combustion engine.

BACKGROUND ART

In use, gas sensor devices which measure the concentration of a given gas component such as nitrogen oxide (NOx) are arranged in an exhaust pipe of an internal combustion engine. In the gas sensor devices, voltage is applied between a pair of electrodes disposed on a front and a back surface of a solid electrolyte body to regulate the concentration of oxygen in the exhaust gas, i.e., a measurement gas to be less than or equal to a given concentration. In order to enhance the accuracy in determining the concentration of the given gas component, the concentration of oxygen which still remains after the concentration of oxygen is regulated is measured or further regulated.

For instance, Japanese Patent First Publication No. 2002-310987 discloses a gas sensor device which regulates the concentration of oxygen in the measurement gas using an oxygen pump cell made by a pair of electrodes disposed on a solid electrolyte body and measures the concentration of oxygen remaining in the measurement gas using an oxygen monitor cell made of a pair of electrodes disposed on the solid electrolyte body. The gas sensor device works to measure the concentration of the given gas component in the measurement gas using a sensor cell made of a pair of electrodes disposed on the solid electrolyte body. An ion current value representing the concentration of residual oxygen is subtracted from an oxygen ion current value, as derived as indicating the concentration of the given gas component to reduce effects of the residual oxygen on determination of the concentration of the given gas component.

SUMMARY OF THE INVENTION

Problem to be Solved by the Invention

However, in the gas sensor device, as taught in Japanese Patent First Publication No. 2002-310987, material of the electrodes of the oxygen monitor cell is different from that of the electrodes of the sensor cell. This results in a difference between the oxygen monitor cell and the sensor cell in output sensitivity to the concentration of oxygen or reduction in sensitivity to the concentration of oxygen which arises from the aging thereof. Such a difference will be a factor causing an error in measuring the concentration of a given gas component in the gas sensor device.

It is, therefore, impossible to further enhance the accuracy in measuring the concentration of the given gas component by subtracting the oxygen ion current value derived in the oxygen monitor cell from the oxygen ion concentration value derived in the sensor cell.

The present invention was made in view of the above problem to provide a gas sensor device which has a simple structure and increases the accuracy in measuring the concentration of a given gas component.

Means for Solving the Problem

According to one embodiment of this disclosure, there is provided a given gas concentration measuring method of measuring a concentration of a given gas component in exhaust gas flowing in an exhaust pipe of an internal combustion engine using a gas sensor device which is arranged in an exhaust pipe of an internal combustion engine to measure a concentration of a given gas component in exhaust gas flowing in the exhaust pipe. The gas sensor device comprises: (a) a solid electrolyte body which has oxygen ion conductivity; (b) a measurement gas space which is formed on one of surfaces of the solid electrolyte body and into which the exhaust gas is introduced as a measurement gas through a diffusion resistor; (c) a reference gas space which is formed on the other surface of the solid electrolyte body and into which a reference gas is introduced; (d) a pump cell which has a pump electrode disposed on a surface of the solid electrolyte body which faces the measurement gas space, the pump cell being designed so that voltage is applied between the pump electrode and a reference electrode disposed on a surface of the solid electrolyte body which faces the reference gas space to regulate a concentration of oxygen in the measurement gas space; and (e) a sensor cell which has a sensor electrode disposed on the surface of the solid electrolyte body which faces the measurement gas space downstream of the pump electrode in a flow direction of the measurement gas, the sensor cell working to measure an oxygen ion current flowing between the sensor electrode and the reference electrode. An oxygen ion current value measured by the sensor cell a given period of time after spraying of fuel into the internal combustion engine is interrupted is subtracted from an oxygen ion current value, as measured by the sensor cell when the fuel is being sprayed into the internal combustion engine to derive the concentration of the given gas component.

Beneficial Effects of the Invention

The above described gas concentration measuring method uses the sensor cell to reduce effects of the concentration of oxygen remaining in the measurement gas whose concentration of oxygen has already been regulated by the pump cell on the accuracy in determining the concentration of the given gas component.

Specifically, the gas sensor device is designed to subtract the oxygen ion current value, as measured by the sensor cell a given period of time after spraying of fuel into the internal combustion engine is interrupted, from the oxygen ion current value, as measured by the sensor cell when the fuel is being sprayed into the internal combustion engine, to derive the concentration of the given gas component. This causes the oxygen ion current value when the concentration of the given gas component is not being measured by the sensor cell to be subtracted from the oxygen ion current value when the concentration of the given gas component is being measured by the sensor cell, thereby reducing the effects of the concentration of oxygen remaining in the measurement gas on the accuracy in determining the concentration of the given gas component.

The reduction of the effects of the concentration of residual oxygen eliminates the need for an additional cell such as an oxygen monitor cell which is equipped with monitor electrodes different in material from the sensor electrode. This eliminates factors causing errors when the oxygen monitor cell is used and also results in a simplified structure of the gas sensor device.

The above described gas concentration measuring method, therefore, improves the accuracy in measuring the concentration of the given gas component.

EMBODIMENT FOR CARRYING OUT THE INVENTION

A preferred embodiment of a given gas concentration measuring method will be described below.

In the above given gas concentration measuring method, the above given period of time is determined based on a time lag it takes for exhaust gas to travel from an internal combustion engine to the gas sensor device in an exhaust pipe in view of a flow rate of the exhaust gas in the internal combustion engine.

The above measurement gas space is made up of a first gas space in which the above pump cell is disposed and a second gas space in which the above sensor cell is disposed. The first gas space and the second gas space may communicate with each other through a barrier wall, as defined by a smaller cross section of space in a direction of flow of the measurement gas, or a porous body which admits gas to flow therethrough.

The above arrangement makes it possible for the measurement gas to stay as long as possible in the first gas space in which the pump electrode is disposed. It is also possible to enhance the accuracy in regulating the concentration of oxygen in the measurement gas using the pump cell. This results in further improved accuracy in determining the concentration of the given gas component in the given gas concentration measuring method.

The second gas space has disposed therein an auxiliary pump cell which works to regulate the oxygen concentration in the above measurement gas after being regulated in oxygen concentration by the above pump cell. The auxiliary pump cell may have an auxiliary pump electrode disposed on a surface of the above solid electrolyte body which faces the above the measurement gas space. The voltage may be applied between the auxiliary pump electrode and the above reference electrode to regulate the oxygen concentration in the above second gas space.

The above case further improves the accuracy in regulating the oxygen concentration in the measurement gas using the auxiliary pump cell. This leads to further improved accuracy in detecting the concentration of the given gas component in the given gas concentration measuring method.

EMBODIMENTS

The gas sensor device 1 will be described below with reference to the drawings.

First Embodiment

The gas sensor device 1 is disposed in an exhaust pipe of an internal combustion engine and used to measure the concentration of a given gas component in the exhaust gas flowing in the exhaust pipe.

Figure 1:
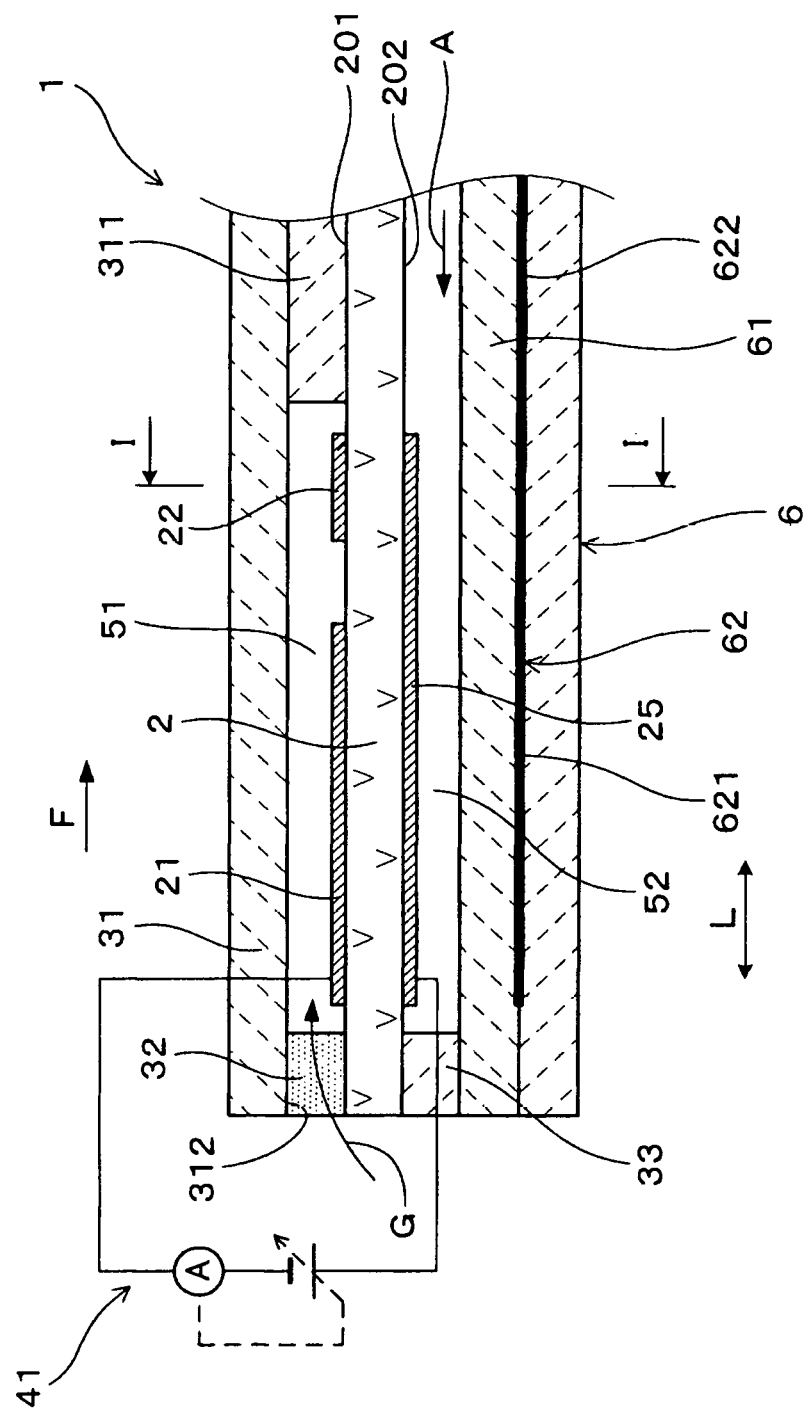
FIG. 1 is a sectional view which illustrates a gas sensor device according to the first embodiment.
Figure 2:
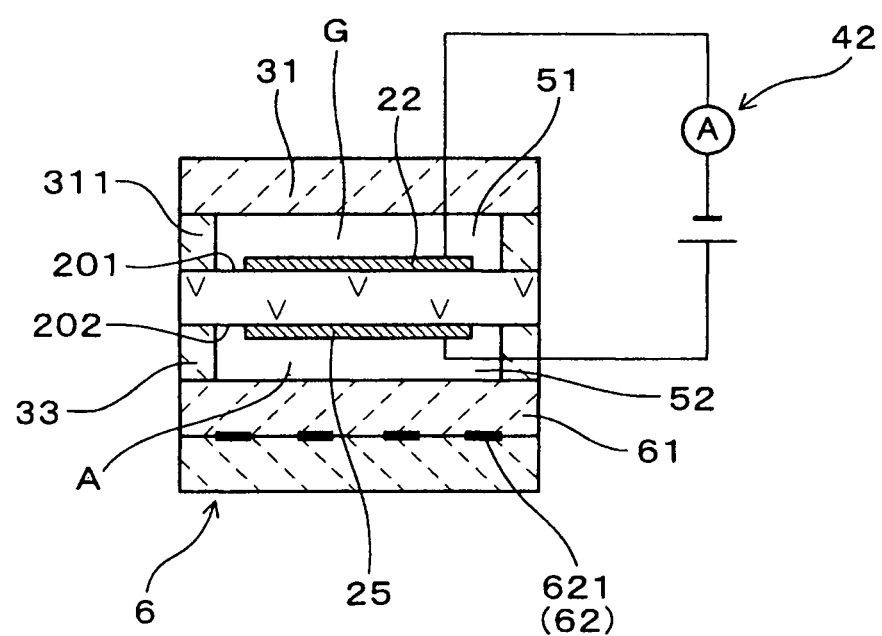
FIG. 2 is a sectional view, as taken along the line I-I in FIG. 1 in the first embodiment.

The gas sensor device 1, as illustrated in FIGS. 1 and 2, includes the solid electrolyte body 2 having an oxygen ion conductivity, the measurement gas space (chamber) 51, the reference gas space 52, the pump cell 41, and the sensor cell 42. The measurement gas space 51 is formed on one of surfaces of the solid electrolyte body 2. The measurement gas space 51 is a space into which exhaust gas is introduced through the diffusion resistor 32 as the measurement gas G. The reference gas space 52 is formed on the other surface of the solid electrolyte body 2 and defined as a space into which the reference gas A is introduced.

The pump cell 41 has the pump electrode 21 which is arranged on the surface 201 of the solid electrolyte body 2 which faces the measurement gas space 51. The pump cell 41 works to apply voltage between the pump electrode 21 and the reference electrode 25 which is disposed on the surface 202 of the solid electrolyte body 2 which faces the reference gas space 52 to regulate the concentration of oxygen in the measurement gas space 51. The sensor cell 42 has the sensor electrode 22 which is disposed on the surface 201 of the solid electrolyte body 2 which faces the measurement gas space 51. The sensor electrode 22 is located downstream from the pump electrode in a direction F in which the measurement gas G flows. The sensor cell 42 works to measure an oxygen ion current flowing between the sensor electrode 22 and the reference electrode 25.

Figure 3A:
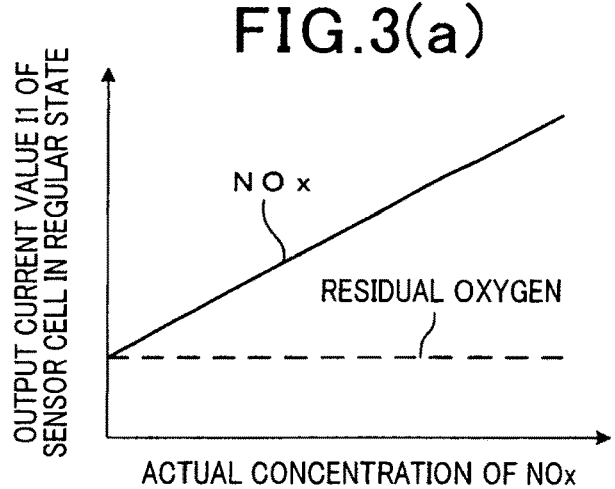
FIG. 3(a) is a graph which represents a relation between the concentration of NOx and an output current value of a sensor cell in a regular state in the first embodiment.
Figure 3B:
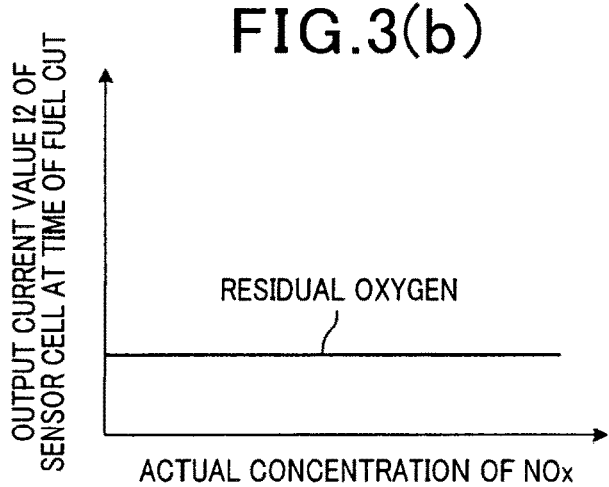
FIG. 3(b) is a graph which represents a relation between the concentration of NOx and an output current value of a sensor cell at a time of fuel cut in the first embodiment.
Figure 3C:
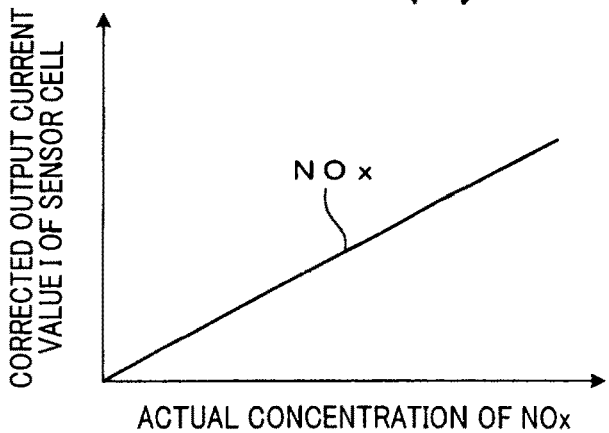
FIG. 3(c) is a graph which represents a relation between the concentration of NOx and a corrected output current value of a sensor cell in the first embodiment.

The gas sensor device 1, as illustrated in FIGS. 3(a) to 3(c), works to determine the concentration of the given gas component based on the oxygen ion current value I, as corrected by subtracting the oxygen ion current value I2 from the oxygen ion current value I1. The oxygen ion current value I1 is measured by the sensor cell 42 when fuel is being sprayed into the internal combustion engine. The oxygen ion current I2 is measured by the sensor cell 42 a given period of time after the spraying of fuel into the internal combustion engine is stopped.

The gas sensor device 1 will be described below in detail with reference to FIGS. 1 to 5.

In use, the gas sensor device 1 which is disposed inside a cover is installed in an exhaust pipe of an automotive vehicle. The measurement gas G is exhaust gas passing through the exhaust pipe. The gas sensor device 1 is used to measure the concentration of NOx (nitrogen oxide) contained in the exhaust gas as the given gas component. The gas sensor device 1 may measure the concentration of $NH_3$ (ammonia).

The pump electrode 21, the sensor electrode 22, and the reference electrode 25 are, as can be seen in FIG. 1, disposed on the single solid electrolyte body 2. The insulator 31 is stacked through the insulating first spacer 311 on the surface 201 of the solid electrolyte body 2 which faces the measurement gas space 51, thereby defining the measurement gas space 51. The heater 6 is also stacked through the insulating second spacer 33 on the surface 202 of the solid electrolyte body 2 which faces the reference gas space 52 to heat the solid electrolyte body 2.

The gas sensor device 1 is, as can be seen in FIG. 1, of a rectangular shape and designed to introduce the measurement gas G from one end thereof in the lengthwise direction L. The diffusion resistor 32 is embedded in an inlet port 312 for the measurement gas G formed in an end portion of the first spacer 311 in the lengthwise direction L. The flow direction of the measurement gas G in the gas sensor device 1 is oriented from one end to the other end of the gas sensor device 1 in the lengthwise direction L.

The diffusion resistor 32 is, as illustrated in FIGS. 1 and 2, made of a porous body which is gas permeable and works to introduce the measurement gas G at a given diffusion rate into measurement gas space 51. The heater 6 has the conductive layer 62 which is disposed in the insulator substrate 61 and through which electric current flows. The conductive layer 62 includes the heating conductive portion 621 which is opposed to the pump electrode 21 and the sensor electrode 22 and a pair of lead portions 622 which connect with ends of the heating conductive portion 621.

The pump cell 41 is equipped with a voltage applying means which works to apply voltage between the pump electrode 21 and the reference electrode 25. The sensor cell 42 is equipped with a current measuring means which works to measure electric current flowing between the sensor electrode 22 and the reference electrode 25.

The solid electrolyte body 2 is a zirconia substrate which has an oxygen ion conductivity. The reference electrode 25 of this embodiment is shared by the pump electrode 21 and the sensor electrode 22 and opposed thereto. The reference electrode 25 may alternatively be provided one for each of the pump electrode 21 and the sensor electrode 22. The pump electrode 21 and the reference electrode 25 made of an oxygen-degradable material such as platinum and gold. The sensor electrode 22 is made of NOx-degradable material such as platinum as well as rhodium.

The operation of the gas sensor device 1 to measure the concentration of the given gas component, i.e., NOx and beneficial advantages of the gas sensor device 1 will be described below.

When the concentration of NOx in the measurement gas G is measured by the gas sensor device 1, the measurement gas G, i.e., the exhaust gas is introduced into the measurement gas space 51 through the diffusion resistor 32. The reference gas A, i.e., air is also introduced into the reference gas space 52.

The voltage is then applied between the pump electrode 21 and the reference electrode 25 of the pump cell 41 to discharge oxygen contained in the measurement gas G from the measurement gas space 51 so as to keep the concentration of oxygen in the measurement gas G in the measurement gas space 51 at a constant oxygen concentration.

Subsequently, the measurement gas G whose concentration of oxygen has been regulated by the pump cell 41 flows to a downstream side of the measurement gas space 51. In the sensor cell 42, the amount of oxygen ion current value I1 that is a function of the concentration of NOx and residual oxygen flows, as illustrated in FIG. 3(a), between the sensor electrode 22 and the reference electrode 25.

The gas sensor device 1 uses a condition where NOx is hardly emitted from the internal combustion engine to reduce effects of the concentration of residual oxygen in the measurement gas space 51 on the accuracy in measuring the concentration of NOx. Specifically, when NOx is hardly emitted from the internal combustion engine (i.e., in a fuel cut condition), the oxygen ion current value I2, as illustrated in FIG. 3(b), flows between the sensor electrode 22 and the reference electrode 25 as a function of the concentration of oxygen. The pump cell 41 is controlled to keep the concentration of oxygen in the measurement gas G constant at all times. The oxygen ion current value I2 in the sensor cell 42 at the time of fuel cut is, therefore, substantially identical with the oxygen ion current value I2' in the sensor cell 42 when fuel is burned in the internal combustion engine.

The oxygen ion current value I2 in the sensor cell 42 at the time of fuel cut is, therefore, defined as the oxygen ion current value I2, as measured by the sensor cell 42 a given period of time after the spraying of fuel is interrupted in the internal combustion engine. The oxygen ion current value I1 in the sensor cell 42 in a regular state is defined as the oxygen ion current value I1, as measured as a function of the concentration of NOx and the concentration of residual oxygen when fuel is sprayed into the internal combustion engine.

In the gas sensor device 1, the oxygen ion current value I2, as measured by the sensor cell 42 the given period of time after the spraying of fuel into the internal combustion engine is interrupted, is subtracted from the oxygen ion current value I1, as measured by the sensor cell 42 in the regular state where the fuel is sprayed into the internal combustion engine, to derive, as illustrated in FIG. 3(a), the oxygen ion current I after corrected.

In the above way, the oxygen ion current value when the concentration of NOx is not being measured by the sensor cell 42 is subtracted from the oxygen ion current value when the concentration of NOx is being measured by the sensor cell 42, thereby reducing the effects of the concentration of oxygen remaining in the measurement gas G on the accuracy in determining the concentration of NOx.

The reduction of the effects of the concentration of residual oxygen eliminates the need for an additional cell such as an oxygen monitor cell which is equipped with monitor electrodes different in material from the sensor electrode 22. This eliminates factors causing errors when the oxygen monitor cell is used and also results in a simplified structure of the gas sensor device 1.

The gas sensor device 1 of this embodiment, therefore, enhances the accuracy in measuring the concentration of NOx.

Second Embodiment

Figure 4:
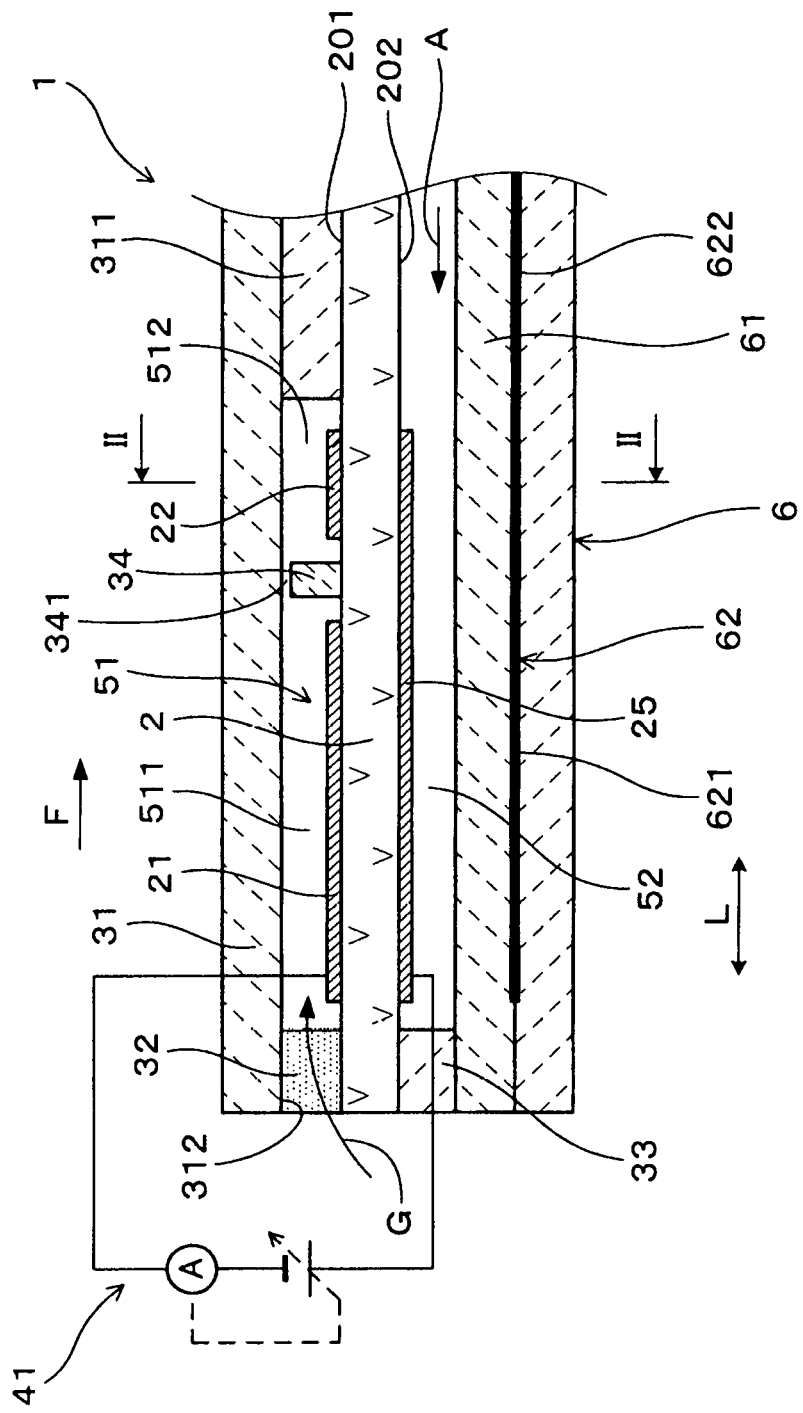
FIG. 4 is a sectional view which illustrates a gas sensor device according to the second embodiment.
Figure 5:
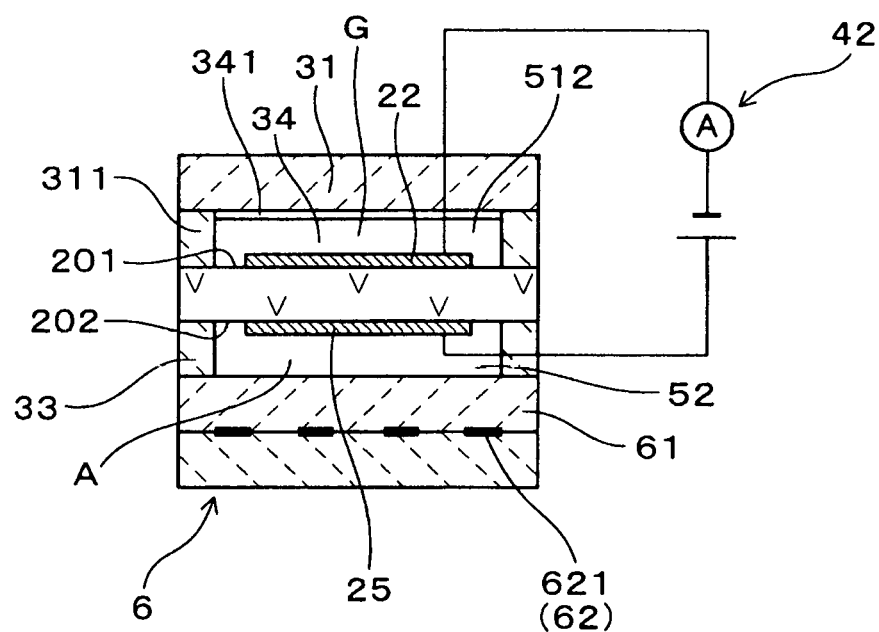
FIG. 5 is a sectional view, as taken along the line II-II in FIG. 4, according to the second embodiment.

The gas sensor device 1 of this embodiment, as illustrated in FIGS. 4 and 5, has the measurement gas space 51 includes a first gas space 511 in which the pump cell 41 is disposed and a second gas space 512 in which the sensor cell 42 is disposed.

The first gas space 511 is formed on an end side in the lengthwise direction L where the diffusion resistor 32 is installed. The second gas space 512 is formed in the other end in the lengthwise direction L adjacent the first gas space 511. The measurement gas G is made to stay as long as possible in order for residual oxygen in the measurement gas G to hardly flow toward the sensor electrode 22 of the second gas space 512.

The first gas space 51 and the second gas space 512 communicate with each other and are separate from each other by the barrier wall 34 which decreases a spatial cross section in the flow direction F of the measurement gas G. The barrier wall 34 extends from the surface 201 of the solid electrolyte body 2 which faces the measurement gas space 51. The slit 342 (i.e., a gap) through which the measurement gas G passes is formed between the insulator 31 and an end surface of the barrier wall 34.

The first gas space 511 and the second gas space 512 may alternatively be isolated from each other by a gas permeable porous body instead of the barrier wall 34. The porous body may be disposed to fully isolate between the first gas space 511 and the second gas space 512.

The other arrangements of the gas sensor device 1 of this embodiment are identical with those in the first embodiment. The reference numbers in the drawings are identical with those in the first embodiment. The gas sensor device 1 of this embodiment offers the same beneficial advantages as in the first embodiment.

Third Embodiment

Figure 6:
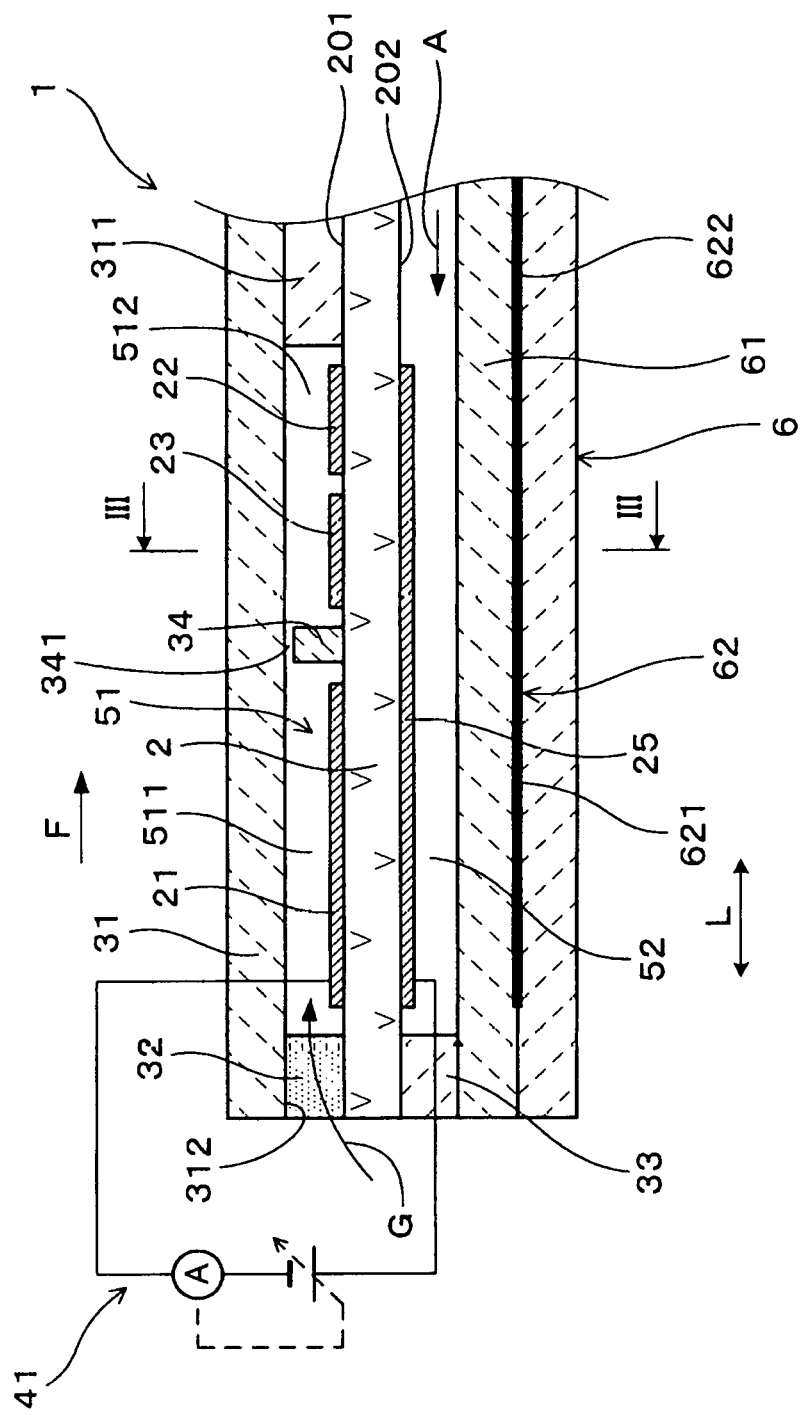
FIG. 6 is a sectional view which illustrates a gas sensor device according to the third embodiment.
Figure 7:
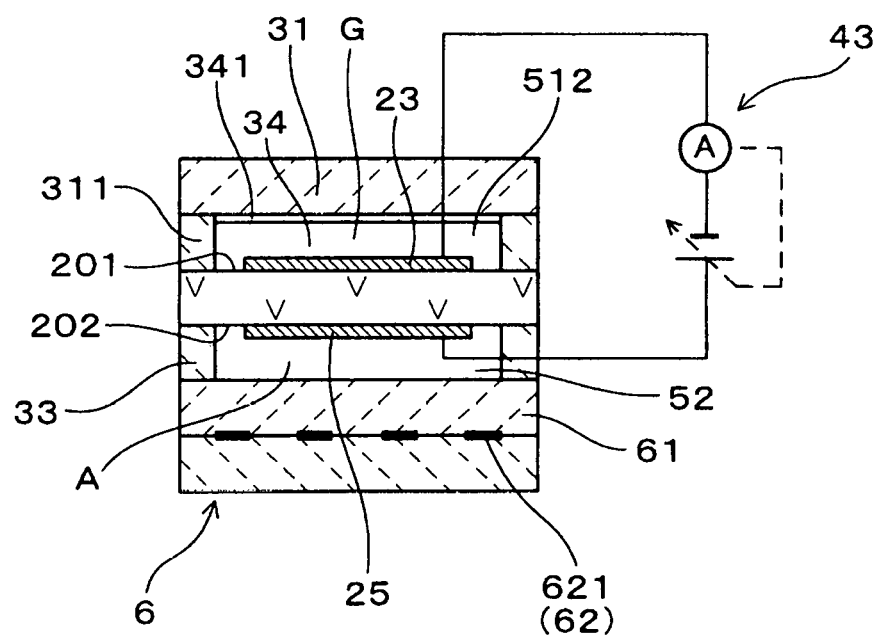
FIG. 7 is a sectional view, as taken along the line in FIG. 6, according to the third embodiment.

The gas sensor device 1 of this embodiment, as illustrated in FIGS. 6 and 7, has the auxiliary pump cell 43 disposed in the second gas space 512. The auxiliary pump cell 43 works to regulate the concentration of oxygen in the measurement gas G whose concentration of oxygen has already been regulated by the pump cell 41.

The auxiliary pump cell 43 includes the auxiliary pump electrode 23 disposed on the surface 201 of the solid electrolyte body 2 which faces the measurement gas space 51. The voltage is applied between the auxiliary pump electrode 23 and the reference electrode 25 to regulate the concentration of oxygen in the second gas space 512. The auxiliary pump electrode 23 is located upstream of the sensor electrode 22 within the second gas space 512 in the flow direction F of the measurement gas G. The auxiliary pump cell 43 works to additionally regulate the concentration of residual oxygen in the measurement gas G, thereby further enhancing the accuracy in determining the concentration of NOx.

The other arrangements of the gas sensor device 1 of this embodiment are identical with those in the first embodiment. The reference numbers in the drawings are identical with those in the first embodiment. The gas sensor device 1 of this embodiment offers the same beneficial advantages as in the first embodiment.

What is claimed is:

1. A method of measuring a concentration of a given gas component in exhaust gas flowing in an exhaust pipe of an internal combustion engine using a gas sensor device which is arranged in the exhaust pipe of the internal combustion engine, the gas sensor device comprising:
    a solid electrolyte body which has oxygen ion conductivity;
    a measurement gas space which is formed on one of surfaces of the solid electrolyte body and into which the exhaust gas is introduced as a measurement gas through a diffusion resistor;
    a reference gas space which is formed on the other surface of the solid electrolyte body and into which a reference gas is introduced;
    a pump cell which has a pump electrode disposed on a surface of the solid electrolyte body which faces the measurement gas space, the pump cell being designed so that voltage is applied between the pump electrode and a reference electrode disposed on a surface of the solid electrolyte body which faces the reference gas space to regulate a concentration of oxygen in the measurement gas space; and
    a sensor cell which has a sensor electrode disposed on the surface of the solid electrolyte body which faces the measurement gas space downstream of the pump electrode in a flow direction of the measurement gas, the sensor cell working to measure an oxygen ion current flowing between the sensor electrode and the reference electrode,
    wherein an oxygen ion current value, as measured by the sensor cell a given period of time after spraying of fuel into the internal combustion engine is interrupted, is subtracted from an oxygen ion current value, as measured by the sensor cell when the fuel is being sprayed into the internal combustion engine to derive the concentration of the given gas component.

2. The method as set forth in claim 1, wherein the measurement gas space includes a first gas space in which the pump cell is disposed and a second gas space in which the sensor cell is disposed, and in that the first gas space and the second gas space communicate with each other and are separate from each other by a barrier wall which decreases a spatial cross section in the flow direction of the measurement gas or a gas permeable porous body.

3. The method as set forth in claim 2, wherein in the second gas space, an auxiliary pump cell which works to further regulate a concentration of oxygen in the measurement gas whose concentration of oxygen has already been regulated by the pump cell, and in that the auxiliary pump cell has an auxiliary pump cell disposed on the surface of the solid electrolyte body which faces the measurement gas space, voltage being applied between the auxiliary pump electrode and the reference electrode to regulate the concentration of oxygen in the second gas space.

* * * * *